(12) United States Patent
Wang et al.

(10) Patent No.: US 6,756,526 B2
(45) Date of Patent: Jun. 29, 2004

(54) DROUGHT TOLERANT PLANTS AND METHODS OF INCREASING DROUGHT TOLERANCE IN PLANTS

(75) Inventors: Xuemin Wang, Manhattan, KS (US); Yongming Sang, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 281 days.

(21) Appl. No.: 09/817,869

(22) Filed: Mar. 26, 2001

(65) Prior Publication Data

US 2003/0074692 A1 Apr. 17, 2003

(51) Int. Cl.$^7$ .......................... C12N 15/82; C12N 15/90
(52) U.S. Cl. ...................... 800/290; 800/278; 800/286
(58) Field of Search .................. 435/410, 419, 435/468; 800/278, 285, 286, 295, 298, 289

(56) References Cited

PUBLICATIONS

Sang et al., Plant J., Oct. 2001, vol. 28, pp. 135–144.*
Fan, Lu, Suqin Zheng, and Xuemin Wang ; "Antisense Suppression of Phospholipase Dα Retards Abscisic–Acid– and Ethylene–Promoted Senescence of Postharvest Arabidopsis Leaves," *The Plant Cell*, vol. 9, 2183–2196, Dec. 1997.
Fan, Lu, Suqin Zheng, Decai Cui, and Xuemin Wang; "Subcellular Distribution and Tissue Expression of Phospholipase Dα, Dβ, and Dγ in Arabidopsis," *Plant Physiology*, vol. 119, 1371–1378, Apr. 1999.
Frank, Wolfgang, Teun Munnik, Katja Kerkmann, Francesco Salamini, and Dorothea Bartels;"Water Deficit Triggers Phospholipase D Activity in the Resurrection Plant *Craterostigma plantagineum*," *The Plant Cell*, vol. 12, 111–123, Jan. 2000.
Jacob, Tobias, Sian Ritchie, Sarah M. Assmann, and Simon Gilroy; "Abscisivc acid signal transduction in guard cells is mediated by phospholipase D activity," *PNAS*, vol. 96, No. 21, 12192–12197, Oct. 12, 1999.
Pappan, Kirk, Suqin Zheng, and Xuemin Wang; "Identification and Characterization of a Novel Plant Phospholipase D That Requires Polyphosphoinositides and Submicromolar Calcium for Activity in Arabidopsis," *The Journal of Biological Chemistry*, vol. 272, No. 11, 7048–7054, Mar. 14, 1997.

Ryu, Stephen B., and Xuemin Wang; "Activation of Phospholipase D and the Possible Mechanism of Activation in Wound–Induced LIpid Hydrolysis in Castor Bean Leaves," *BBA Biochimica et Biophysica Acta*, 1303:243–250 (1996).

Wang, Xuemin; "The Role of Phospholipase D in Signaling Cascades," *Plant Physiology*, vol. 120, 645–651, Jul. 1999.

Wasteneys, G.O., J. Willingale–Theune, and D. Menzel; "Freeze Shattering: A Simple and Effective Method for Permeabilizing Higher Plant Cell Walls," *Journal of Microscopy*, vol. 188, Pt. 1, 51–61, Oct. 1997.

Wang et al. "Characterization of Phospholipase D–Overexpressed and Suppressed Transgenic Tobacco and Arabidopsis," In *Physiology, Biochemistry and Molecular Biology of Plant Lipids*, 345–347 (1997), Williams, J.P., Khan, M.U., and Lem, N. W. Eds.

Xu, Liwen, Suqin Zheng, Ling Zheng, and Xuemin Wang; "Promoter Analysis and Expression of a Phosphloipase D Gene from Castor Bean," *Plant Physiol.*, vol. 115, 387–395 (1997).

Zheng, Li, Ramaswamy Krishnamoorthi, Michal Zolkiewski, and Xuemin Wang; "Distinct $Ca^2$ Binding Properties of Novel C2 Domains of Plant Phospholipase Dα and β," *The Journal of Biological Chemistry*, vol. 275, 19700–19706, Jun. 30, 2000.

Dyer et al., Cloning and Nucleotide Sequence of a CDNA (Accesson No. U36381) Encoding Phospholipase D from Arabidopsis; 109 Plant Physiol 1497 (1995).

Qin, W. et al., Molecular Heterogeneity of Phospholipase D (PLD); 272 J. Biol. Chem. 28267–28273 (1997).

Thimann, K. et al., Relation Between Leaf Senescence and Stomatal Closure: Senescence in Light; *Proc. Natl. Acad. Sci. USA*, 76:2295–2298 (1979).

* cited by examiner

*Primary Examiner*—Ashwin Mehta
(74) *Attorney, Agent, or Firm*—Hovey Williams LLP

(57) ABSTRACT

Methods of growing plants having modified transpiration rates are provided. Such methods permit more efficient water conservation through regulation of stomatal closure responses. Accordingly, modified plants can be grown in areas which were previously unsuitable for growth and plants which can withstand drought conditions can be grown.

34 Claims, 13 Drawing Sheets

DROUGHT TOLERANT PLANTS AND METHODS OF INCREASING DROUGHT TOLERANCE IN PLANTS

FEDERALLY SPONSORED RESEARCH OR DEVELOPMENT

This invention was made with government support of the USDA (Grant No. 97-35304-4877) and NSF (Grant No. IBN 9808729). The government has certain rights in the invention.

SEQUENCE LISTING

A printed Sequence Listing accompanies this application, and has also been submitted with identical contents in the form of a computer-readable ASCII file on CDROM.

BACKGROUND OF THE INVENTION

1. Field of the Invention

The present invention generally relates to the field of plants. More particularly, the present invention involves plant responses to stress and methods of altering these responses. Still more particularly, the present invention involves transgenic plants which have altered expression of phospholipase D which thereby affects plant transpiration, respiration, and bioremediation. Finally, the present invention involves breeding and selecting such transgenic plants for growth in stress-prone areas.

2. Description of the Prior Art

Terrestrial plants lose water primarily via stomata, which are pores defined by pairs of guard cells. These guard cells and stomata are located throughout the epidermis of plant stems and leaves. When subjected to heat and light, each pair of guard cells separates, thereby forming the stomata therebetween wherein plant transpiration and respiration occur. During respiration, when the stomata are open, carbon dioxide and oxygen enter and exit the leaf. When carbon dioxide enters, it participates in photosynthesis and releases oxygen as a waste product. The oxygen then passes out of the leaf through the open stomata. Additionally, oxygen also enters the leaf and takes part in respiration, thereby forming carbon dioxide as a waste product. This carbon dioxide exits the leaf via the stomata.

During transpiration, water, in the form of vapor, exits the stomata. It has been determined that more than 90% of the water loss in terrestrial plants is through the stomata. Plants minimize water loss and evaporation through the stomata in a number of ways. For example, more stomata are located on the underside of a leaf (the side of the leaf which faces the ground) than on the upper side. Stomata also close at night in response to a decreased amount of light, thereby increasing water conservation. Stomata also close in response to decreasing amounts of available water. This stomatal closure is crucial for maintaining hydration status in leaves and therefore contributes to plant survival during times of drought.

Phospholipase D (PLD) hydrolyzes phospholipids, generating phosphatidic acid (PA) and free head groups. This enzyme has been implicated in various processes, including signal transduction, membrane trafficking, cytoskeletal rearrangement, and membrane degradation. Suppression of a PLD in Arabidopsis has been shown to decrease the rate of abscisic acid (ABA)-promoted senescence in detached leaves. Other experiments have shown that the addition of phosphatidic acid (PA), a potential PLD reaction product, to protoplasts of barley aleurone and *Vicia faba* guard cells partially mimicked the effect of ABA. Activity and gene expression of PLD also increased in tissues treated with ABA and in plants under water deficit. (Xu, et al. *Promoter Analysis and Expression of a Phospholipase D Gene from Castor Bean*, 115 Plant Physiol 387–395 (1997); Jacob, et al. *Abscisic Acid Signal Transduction in Guard Cells is Mediated By Phospholipase D Activity*, 96 PNAS 12192–12197 (1999); and Frank, et al. *Water Deficit Triggers Phospholipase D Activity in the Resurrection Plant Craterostigma plantagineum*, 12 The Plant Cell 111–123 (2000)).

Because the physiological role of PLD in plants has not been established, the increases in PLD activities and gene expression shown in those studies provide no direct evidence for a role of PLD in plant response to ABA or water deficit. In addition, multiple forms of PLD in plants have been identified recently, and they exhibit different biochemical properties and patterns of expression. This raises a question of which PLD is involved in guard cell regulation. Moreover, the process which promotes stomatal closure during periods of drought stress has not heretofore been determined. Selective regulation and modification of stomatal closure would contribute to the development of drought resistant plants, plants with modified rates of respiration, transpiration, and bioremediation, and plants which react to drought stress in a quicker, more efficient manner.

SUMMARY OF THE INVENTION

The present invention overcomes the problems of the prior art and provides a distinct advance in the state of the art by providing methods of altering drought response in plants, genetically altered plants which have modified stomatal responses in comparison to wild-type plants, methods of selecting for plants having upregulated or down regulated stomatal closure, methods of testing plants for stomatal closure, and methods of differentiating between wild-type plants and plants which have been genetically altered according to the present invention.

It has now been determined that the hormone abscisic acid (ABA) promotes stomatal closure and that phospholipase D (PLD) participates in the regulation of stomatal closure induced by ABA and water stress. Three distinct PLDs, PLDα, PLDβ and PLDγ, have been cloned from Arabidopsis (Dyer et al., 109 Plant Physiol 1497 (1995); Pappan et al., 272 J. Biol. Chem. 7048–7054 (1997); Qin et al., 272 J. Biol. Chem. 28267–28273 (1997)). PLDα is expressed in Arabidopsis guard cells, and the introduction of a PLDα antisense gene abrogated its expression. The sequence of the PLDα antisense gene is provided herein as Sequence ID No. 1. Preferably, sequences having at least about 60% sequence similarity or 50% sequence identity with SEQ ID No. 1 are introduced into the PLD genome and suppress expression of PLDα. More preferably, such sequences have at least about 70% sequence similarity or 65% sequence identity with SEQ ID No. 1. Most preferably, such sequences have at least about 90% sequence similarity or 85% sequence identity with SEQ ID No. 1. Plants expressing decreased amounts of PLDα also exhibit a decreased sensitivity to ABA as well as impaired stomatal closure. PLDα-depleted plants exhibited an accelerated rate of transpirational water loss and decreased ability to tolerate drought stress. Overexpression of PLDα increased the leaf's sensitivity to ABA in promoting stomatal closure and decreased the rate of transpirational water loss. Thus, PLD plays a crucial role in controlling stomatal movement and the plant's tolerance to water deficit.

To investigate the function of PLD in plant-water relations, the presence of PLDα in Arabidopsis guard cells was determined using immunolabeling with isoform-specific antibodies raised against PLDα. To perform this testing, Arabidopsis plants were grown. After 4–5 weeks of growth, fully expanded Arabidopsis leaves were detached. Epidermal peels were collected from the abaxial side of Arabidopsis leaves immediately following detachments and incubated for 1 hour in a solution containing 5 mM MES-KOH (pH 6.1), 22 mM KCl, and 1 mM $CaCl_2$. The peels were then fixed in 1.5% formaldehyde, 0.5% glutaraldehyde, 0.1 M PIPES, 5 mM EGTA, 2 mM $MgCl_2$, and 0.05% Triton X-100, pH 6.9 for 35 minutes with gentle shaking. The fixed peels were washed in phosphate-buffered saline (PBS) for 30 minutes with three changes of solution. Then they were spread onto microscope slides, blotted to remove excess solution, and freeze-shattered using the methods of Wasteneys, et al., *Freeze Shattering: A Simple and Effective Method for Permeabilizing Higher Plant Cell Walls*, 188 Journal of Microscopy 51–61 (1997), the teachings of which are hereby incorporated by reference. Briefly, epidermal peels were collected from the abaxial side of Arabidopsis leaves immediately following their detachment and incubated for one hour in a solution containing 5 mM MES-KOH (pH 6.1), 22 mM KCl, and 1 mM $CaCl_2$, Next, the peels were fixed and the fixed peels were washed in phosphate-buffered saline (PBS) for 30 minutes with three changes of solution. The peels were spread onto a microscope slide, blotted to remove excess solution, and then sandwiched with another slide with clamps. The slide-peels-slide sandwich was submerged in liquid nitrogen before being removed and quickly placed between two aluminum blocks which were precooled in liquid nitrogen. The aluminum block was pressed quickly with a thumb until some shattering sound was heard. The slide sandwich was open quickly and a few drops of the fixative was added to the peels. The peels were then transferred to a centrifuge tube and incubated with 1% Triton X-100 for 1–2 hours. The peels were spread on to slides and dried overnight. The peels adhered to slides were incubated with an enzyme mixture followed by incubating with a second enzyme. The peels were permeabilized, incubated, and blocked. The peels were incubated with antibodies to PLD isoforms or their respective pre-immune sera at 4° C. overnight, followed by incubation at room temperature. All antibodies were diluted 1:100 in the blocking solution. The slides were rinsed and then incubated for 2 hours with a second antibody (1:50 dilution), which was conjugated to an alkaline phosphatase (Sigma). After rinsing, slides were incubated at room temperature with the phosphatase substrate fast red/naphthol that contained 0.6 mM levamisole to block endogenous AP activity from tissues. The slides were rinsed three times with PBS and sealed for observation and photographing using a microscope.

PLDα was labeled with the PLDα antibody and was clearly detectable in guard cells (FIG. 1, photo A). The red color shown in FIG. 1, photo A indicates positive labeling, resulting from the activity of alkaline phosphatase conjugated to a second antibody, whereas labeling with the PLDα preimmune serum gave negligible background (FIG. 1, photo B). The labeling specificity for PLDα was verified unequivocally by the absence of immunostaining in guard cells from PLDα-depleted plants (FIG. 1, photo C). Antisense suppression of PLDα resulted in a nearly complete loss of PLDα in Arabidopsis leaves, as indicated by the absence of PLDα activity (FIG. 2) and protein (FIG. 3). For FIGS. 2 and 3, both the activity and immunoblot assays used 2,000×g supernatant of total leaf extracts. Proteins (10 mg/lane) were separated on 10% SDS-PAGE, and the PLDα band was marked by an arrow. PLDα presence in guard cells was confirmed using fluorescence confocal imaging and immuno-gold electron microscopy. These results establish that PLDα is localized in guard cells and that the expression of PLDα in guard cells is suppressed in PLDα antisense plants.

The depletion of PLDα in guard cells provides a means of assessing the role of PLD in stomatal movement. Stomatal closure was determined by measuring diffusion resistance using a steady-state porometer. Briefly, detached Arabidopsis leaves were floated with the abaxial side downward in a solution containing 5 mM MES-KOH (pH 6.1), 22 mM KCl, and 1 mM $CaCl_2$ for 1 hour under the same light conditions used for growing plants. Leaves then were incubated without or with ABA at indicated concentrations. ABA was made as a 10 mM stock solution in 5% dimethyl sulfoxide (DMSO), and the same amount of DMSO (0.005%) was also added to the control solution in all treatments. Stomatal aperture of detached leaves was measured as diffusion resistance with a steady state porometer using the method of Thimann and S. O. Satler, *Relation Between Leaf Senescence and Stomatal Closure: Senescence in Light*, 76 Proc. Natl. Acad. Sci. USA, 2295–2298 (1979). For tobacco plants, leaf diffusion resistance was also measured in leaves attached to approximately 2-month-old plants following foliar spraying of ABA at indicated concentrations. Changes in diffusion resistance in response to ABA in both detached and intact leaves were monitored at indicated time intervals. Before drought treatment was imposed, Arabidopsis plants were grown in a greenhouse for 6–8 weeks and watered regularly. Soil water content in each pot was adjusted to approximately the same level before drought treatment. Plants were subjected to drought by withholding irrigation and the soil surface in each pot was covered with plastic wraps to minimize evaporation. Soil moisture in the 0–20 cm soil layer was monitored during drought using a time domain reflectometer. When ABA (10 $\mu$M) was sprayed on plants in some treatments, control groups of plants were sprayed with water in the same amount as for the ABA treatment. Leaves were collected at various times of drought treatment, and leaf water potential ($\psi_w$) was measured with a thermocouple psychrometer.

Under normal growing conditions, PLDα-deficient and wild-type plants grew comparably. No differences occurred in plant size, development, and reproduction, or the size and density of guard cells on leaves. Incubation of leaves with 10 $\mu$M ABA induced stomatal closure, as indicated by an approximately twofold increase in diffusion resistance in wild-type leaves (FIG. 4). The ABA effect persisted for more than 30 minutes in wild-type plants and then decreased. The same ABA treatment had a much smaller effect on stomatal closure in PLDα-suppressed leaves. The ABA-induced increase in diffusion resistance was approximately 50% of that observed in wild-type leaves and returned to the basal level 20 minutes after ABA application. The response to ABA in PLDα-deficient leaves resembled that of the well-characterized, ABA-insensitive mutant abi-1, which is defective in a protein phosphatase 2C involved in ABA signaling in Arabidopsis guard cells. At the range of 0.5–50 $\mu$M ABA tested, the PLDα-depleted leaves exhibited a lower diffusion resistance than that of wild-type (FIG. 5). The 2 $\mu$M concentration of ABA stimulated stomatal closure in wild-type leaves but had no effect in PLDα-suppressed leaves. The effect in wild-type leaves reached a plateau at 10 [M ABA, whereas such a plateau was not observed at 50 $\mu$M ABA in PLDα-suppressed leaves. For each of the graphs in FIGS. 4 and 5, leaves were detached and incubated with the abaxial side down in solutions with different levels of ABA for 20 minutes. Values are means±SE of two experiments. These results indicate that PLDα-depleted leaves were less sensitive to ABA.

To determine whether the impaired stomatal closure compromises the plant's ability to cope with water stress, plants were subjected to progressive drought by withholding irrigation. During drought, PLDα-deficient plants wilted earlier than wild-type plants (FIG. 6). A greater loss of water in leaves was indicated by the lower leaf water potentials in PLDα-deficient plants than in wild-type plants (FIG. 7). By the time 5 days of drought treatment had elapsed, the decrease of water potential was twofold greater in PLDα-deficient than in wild-type leaves. Again, before drought stress was initiated, soil water content in each pot was adjusted to approximately the same level and the soil surface was covered with plastic wrap, so that the water loss from the soil came primarily from leaf transpiration. Measurement of soil water content showed an accelerated decrease with PLDα-deficient plants (FIG. 8), indicating a greater transpirational loss of water in these plants.

Additionally, ABA (10 μM) was sprayed on a set of drought-stressed plants once a day to test its effect on promoting drought resistance in PLDα-depleted and wild-type plants. This treatment enhanced resistance to drought in wild-type plants, as indicated by the maintenance of leaf turgidity during drought (FIG. 6) increased leaf water potential (FIG. 7), and soil water content (FIG. 8). The same ABA treatment had no detectable effect on water loss and drought resistance of PLDα-deficient plants. These data provide in planta evidence that suppression of PLDα decreased plant sensitivity to ABA. This reduction in ABA-induced stomatal closure resulted in increased transpirational water loss in PLDα-deficient plants.

To verify the role of PLD in stomatal closure, PLDα-overexpressing tobacco was used to determine the effect of increased PLDα expression on the rate of water loss and ABA-induced stomatal closure. FIGS. 9–12 illustrate these results showing increased sensitivity to ABA-promoted stomatal closure and decreased water loss in PLDα-overexpressing tobacco. Introduction of a PLDα construct to tobacco resulted in approximately a fivefold increase in PLDα activity (FIG. 9). Expression of the introduced PLDα was attested clearly by the presence of a protein band of slightly smaller molecular weight than the tobacco endogenous PLD (FIG. 9, inset). For this immunoblot, proteins (10 mg/lane) were separated on 10% SDS-PAGE, and PLDα was made visible by staining with alkaline phosphatase. The arrow marks the overexpressed PLDα. Both the activity and immunoblot assays used 2,000×g supernatant of total leaf extracts. The introduced PLDα was expressed in tobacco guard cells. Multiple PLDα-overexpressing lines have been produced, and all grew and developed normally to maturity. Cellular fractionation showed that the introduced PLDα had the same intracellular association as the endogenous PLDα, being present in both soluble and microsomal membrane fractions. The PLDα-elevated and wild-type plants also showed no significant differences in leaf phospholipid content and composition (data not shown). Moreover, these observations indicate that PLDα activity is tightly regulated after translation.

The large size of tobacco leaves permitted measurement of transpirational water loss directly on plants after ABA treatments. As shown in FIG. 10, when leaves were sprayed with 2.5 and 5 μM ABA, stomata closed faster and more tightly in the PLDα-overexpressing than in control plants (tobacco transformed with an empty vector). Leaf diffusion resistance was measured directly on plants that were sprayed with ABA and expressed as percentages of that of plants sprayed with water. Leaf diffusion resistance increased about 80% in PLDα-overexpressing plants while diffusion resistance in leaves of control plants increased only about 30% 20 minutes after ABA application. As shown in FIG. 10, the differences in diffusion resistance between the two genotypes were most noticeable within the first 20 minutes after ABA application and diminished afterwards. These differences indicate that overexpression of PLDα enhances plant sensitivity to ABA and also implies that PLD activation could be a limiting step in the early stages of ABA induced stomatal movement induced by ABA.

To assess water loss from leaves without added ABA, leaves of similar size, age, and positions on PLDα-overexpressing and control plants were detached and measured for decreases in fresh weight. Leaves from PLDα-overexpressing plants exhibited markedly lower rates of water loss than those from control plants under ambient conditions (FIG. 11). The differences occurred within 5 minutes and became more apparent between 20 to 30 minutes following detachment. Values are percentages of the means±SE of three experiments. These results show that overexpression of PLDα promotes stomatal closure induced by ABA and/or water deficit and decreases transpirational water loss.

To further demonstrate the effects of PLDα overexpression, PLDα overexpressing tobacco plants and empty vector-transformed tobacco plants were compared. Six week-old tobacco plants of similar sizes were subjected to drought by withholding irrigation for 15 days in a growth room with cool-white fluorescent lights at 23±2° C. and 45% relative humidity. As shown in FIG. 12, the PLDα overexpressing plants exhibited increased resistance to drought through increased turgidity.

With PLDα-depleted Arabidopsis and PLDα-overexpressing tobacco, the present invention illustrates that PLD constitutes a critical step in ABA signaling and plant response to water stress. A look at the biochemical and cellular properties of PLD may indicate PLD's role in mediating ABA action in stomatal closing. Increasing cytoplasmic $Ca^{2+}$ oscillation is a key step in the ABA signal transduction. Mutation or inhibition of the ABA signaling components, such as protein phosphatase 2C, cADP ribose, protein farnesylation, and phospholipase C, impedes ABA-induced $Ca^{2+}$ oscillation and impairs stomatal closure. $Ca^{2+}$ is a regulator of plant PLD in that it is required for PLD activity and it also promotes PLDα association with membranes as shown by S. B. Ryu and X. Wang, *Activation of Phospholipase D and the Possible Mechanism of Activation in Wound-Induced Lipid Hydrolysis in Castor Bean Leaves,* 1303 Biochimica et Biophysica Acta, 243–250 (1996), the methods and teachings of which are hereby incorporated by reference. PLD binds $Ca^{2+}$ at its N-terminal C2 domain, thereby inducing a conformational change and promoting the protein association with phospholipids. ABA exposure increases PLD activity in guard cells as shown by Zheng, et al., *Distinct $Ca^{2+}$ Binding Properties of Novel C2 Domains of Plant Phospholipase Dα and β,* 275 The Journal of Biological Chemistry 19700–19706 (2000), the methods and teachings of which are hereby incorporated by reference. Thus, PLD could be a target of $Ca^{2+}$ oscillation that activates PLD in guard cells.

PLD activation generates the lipid product PA which, when applied to guard cell protoplasts, results in an increase in ionic efflux. Although the mechanism by which PA mediates cellular effect is unknown in plants, PLD-derived PA can activate protein kinases and lipid kinases in animal systems. In particular, PA is a potent stimulator of phosphatidylinositol 5-kinases for the production of phosphatidylinosotol 4,5-bisphosphate, which is a substrate for PI-PLC and also is essential for membrane trafficking and cytoskeletal dynamics. Active membrane trafficking and cytoskeletal rearrangements have been implicated in stomatal movement. In addition, PA may carry out its cellular effect via membrane structural alteration. It is a nonlamellar lipid and favors the formation of hexagonal phase II in the presence of calcium. The formation of PA and lysoPA occurs specifically at the neck of a budding synaptic vesicle and is required in membrane budding.

Thus, the present invention also includes methods of creating transformed plants by recombinantly altering the genome of the plants such that their PLDα expression is altered when compared to a baseline level of PLDα expression in wild type plants. To determine whether or not the genome alteration has effected stomatal closure characteristics, such characteristics are determined. In some instances, the genome alteration results in an up-regulation of PLDα expression and in other cases results in a down-regulation of PLDα expression. A preferred method of up-regulating PLDα expression includes introducing an insert which codes for PLDα. Preferably the insert includes a promoter and PLDα encoding sequences. The preferred PLDα coding sequence is included herein as SEQ ID No. 2. Preferably, sequences having at least about 60% sequence similarity or 50% sequence identity to SEQ ID No. 2 are used to up-regulate PLDα expression by being introduced into the PLD genome. More preferably, such sequences have at least about 70% sequence similarity or 65% sequence identity with SEQ ID No. 2. Most preferably, such sequences have at least about 90% sequence similarity or 85% sequence identity with SEQ ID No. 2. The promoter used is preferably a constitutive promoter and a particularly preferred promoter used to control the inserted sequence is the 35S promoter from the cauliflower mosaic virus. Of course, other promoters such as the ubiquitin promoter would reasonably be expected to work in a similar fashion for purposes of the present invention. These types of promoters provide high levels of expression of heterologous genes in a variety of different cell and tissue types of many dicot and monocot plant species.

Stomatal closure characteristics can be tested in a variety of ways. For example, the transpiration rate of plants can be tested as can the plant's diffusion resistance. Additionally, testing conditions can be varied such that the conditions under which the plants are grown are not conducive to the growth of unmodified or untransformed plants. A preferred testing condition includes subjecting the plants to drought conditions or excessive water conditions. Another form of testing stomatal closure characteristics includes observing the turgidity of plants. This type of observation provides an easily observable phenotypic trait of plants which is directly related to stomatal closure.

The present invention also provides methods of growing transformed plants in locations having unsuitable water and growth conditions for untransformed plants. These methods generally include the steps of recombinantly altering the genome of the plant in an effort to change the level or amount of PLD expressed by the plant, testing water consumption levels of the plant in order to determine if the genome alterations permit plant growth in the unsuitable locations, and planting the progeny of the plant in the conditions which were unsuitable for growth of untransformed plants. Again, preferred alterations are similar to the ones described above for testing the stomatal closure characteristics of plants after genome alteration. By testing the water consumption level of the plant, it will become apparent whether or not the resulting plant and its progeny will be adapted to live in either an environment which has too much soil moisture or, alternatively, too little soil moisture to support normal plant growth. The plant progeny which are adapted for and conditions, as a result of the alteration of the genome, will grow in areas which were previously too dry for plants with unaltered genomes. Conversely, plant progeny which have altered genomes which have increased levels of water consumption (and transpiration) will be able to grow in environments which had previously had too much moisture in the soil to support the growth of plants with unmodified or unaltered genomes. Testing methods for growth of progeny will include testing transpiration rate, diffusion resistance, effects of abscisic acid exposure, effects of drought conditions, and effects of overly wet conditions. Phenotypic testing methods will include observing the plant's turgidity.

Finally, the present invention provides methods of growing transformed plants which have modified stomatal closure responses to water availability in comparison to untransformed plants. Untransformed plants exhibit a baseline stomatal closure response while plants which have been successfully transformed, have stomatal closure responses which differ from that baseline. For the transformed plants, the genome is recombinantly altered in an effort to change the stomatal closure responses and the resultant plants are tested for their stomatal closure responses and then compared to those of untransformed plants to determine whether or not the transformed plant has modified stomatal closure responses. Again, it is preferred to use the same experimental and modifications to these plants as previously described.

In conclusion, the present results demonstrate that PLD plays a crucial role in plant transpiration. Through targeted manipulation of the specific PLD sequence in guard cells permits generation of plants with decreased water consumption and enhanced tolerance to water stress. Alternatively, manipulation of PLD expression may promote increased rates of plant transpiration and be more efficient in bioremediation.

BRIEF DESCRIPTION OF THE DRAWINGS

The patent or application file contains at least one drawing executed in color. Copies of this patent or application with color drawings will be provided by the U.S. Patent and Trademark Office upon request and payment of the necessary fee.

DETAILED DESCRIPTION OF THE PREFERRED EMBODIMENT

Figure 1A:
FIG. 1 is a series of photos showing immunolabeling of PLDα in Arabidopsis guard cells wherein photo A shows Arabidopsis wild-type guard cells labeled with PLDα antibody; photo B shows Arabidopsis wild-type guard cells labeled with preimmune serum; and photo C shows PLDα-suppressed Arabidopsis guard cells labeled with PLDα antibody.

The following examples set forth preferred embodiments and methods of the present invention. It is to be understood, however, that these examples are provided by way of illustration and nothing therein should be taken as a limitation upon the overall scope of the invention.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. et al., eds., M. Stockton Press, New York (1991); and Carillo, H., et al. Applied Math., 48:1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403–410 (1990). The BLASTX program is publicly available from NCBI and other sources (BLAST Manual, Altschul, S. et al., NCVINLM NIH Bethesda, Md. 20894, Altschul, S. F. et al., J. Molec. Biol., 215:403–410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence maybe deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, "sequence similarity", as used herein, also refers to a method of determining the relatedness of two sequences. To determine sequence similarity, two or more sequences are optimally aligned as described above, and gaps are introduced if necessary. However, in contrast to "sequence identity", conservative amino acid substitutions are counted as a match when determining sequence similarity. In other words, to obtain a polypeptide or polynucleotide having 95% sequence similarity with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A "conservative substitution" refers to the substitution of an amino acid residue or nucleotide with another amino acid residue or nucleotide having similar characteristics or properties including size, charge, hydrophobicity, etc., such that the overall functionality does not change significantly.

Isolated" means altered "by the hand of man" from its natural state., i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Transformation" as used herein, refers to the uptake and incorporation of DNA fragments or plasmids by a cell as well as the subsequent recombination of part or all of that DNA into the cell's genome.

"Closure characteristics" means traits, qualities, or properties of stomata as they open to increase transpiration and close to decrease transpiration. Such characteristics include rate of closure, duration of closure, response to stimuli, and the cascade of events leading up to the closure or opening of stomata.

"Unsuitable water and growth conditions" means environmental conditions under which plants having unaltered or unmodified genomes would be unable to grow. Such conditions include soil hydration (either too high or too low), low relative ambient humidity, and high salt content.

"Closure responses" means the activity or inhibition of stomatal closure resulting from stimulation or signaling.

"Drought conditions" means a shortage of moisture in the soil surrounding growing plants which would normally cause damage to growing plants having unmodified or unaltered genomes.

Finally, all references and teachings cited herein which have not been expressly incorporated by reference are hereby incorporated by reference.

EXAMPLE 1

This example describes the procedures used to construct transformed Arabidopsis plants having suppressed levels of PLDα expression.
Materials and Methods:
Transgenic Arabidopsis Production and Growth

*Arabidopsis thaliana* ecotype Columbia was used for this example. Seeds were sown in soil and cold-treated at 4° C. overnight. Plants were grown under 12-hr-light/dark cycles with cool-white fluorescent light of 100 $\mu$mol m$^{-2}$ sec$^{-1}$ at 22±1° C. and 60% relative humidity. The plants at flowering stages were transformed with T-DNAs through *Agrobacterium tumefaciens* strain EHA105 mediated gene transfer. A DNA fragment for the antisense vector was constructed using a 783 bp fragment from the Arabidopsis PLDα cDNA. The DNA sequence of this fragment is provided herein as SEQ ID No. 1. This fragment was cloned into the T-DNA transfer vector pKYLX7 (Schardl et al., 1987), although other T-DNA transfer vectors would also work for purposes of the present invention. The DNA was inserted in the antisense orientation under the control of the cauliflower mosaic virus 35S promoter. The plasmid was transformed into Agrobacterium and then was transferred into Arabidopsis via a vacuum infiltration method (Bechtold et al., 1993). Agrobacterium strain EHA 105 with the T-DNA plasmid was grown overnight at 28° C. in LB medium with 12.5 $\mu$M/ml tetracycline and 30 $\mu$M/ml rifampsin, until culture OD600 reached mid-log to stationary phase. The bacterial culture was spun down and resuspended to OD600=0.6 in 5% sucrose solution. Before dipping, Silwet L-77 was added to a concentration of 0.03% (300 $\mu$l/L) and mixed well. Above-ground parts of flowering plants were submerged in Agrobacterium solution for 2 to 3 seconds with gentle agitation. Dipped plants were placed under a cover overnight. Plants were then transferred to growth chambers and grew to maturity before harvesting the seeds. Transformants were selected using 50 $\mu$M/ml kanomycin on 0.5×MS/0.8% tissue culture agar plates for 7–10 days. Putative transformants were transplanted to soil and tested for the suppression of PLD. The suppression of PLDα was confirmed by assaying PLDα activity and immunoblotting with PLD-isoform-specific antibodies. Total protein from Arabidopsis or tobacco leaves was extracted by grinding in an ice-chilled mortar and pestle with buffer A (50 mM Tris-HCl, pH 7.5, 10 mM KCl, 1 mM EDTA, 0.5 mM PMSF, and 2 mM DTT). The homogenate was centrifuged at 6,000×g for 10 minutes at 4° C. to remove tissue debris, and the resulting supernatant was used for activity assays and immunoblotting. PLD activity was determined based on procedures described previously (Pappan et al., 1997). Total protein from Arabidopsis tissues was extracted by grinding in an ice-chilled mortar and pestle with buffer A containing 50 mM Tris-HCl, pH 7.5, 10 mM KCl, 1 mM EDTA, 0.5 mM PMSF, and 2 mM DTT. The homogenate was centrifuged at 10,000×g for 10 minutes at 4° C. to remove tissue debris, and the supernatant was used for assaying enzyme activity. The assay reaction mixture contained 100 mM MES (pH 6.5), 25 mM CaCl$_2$, 0.5 mM SDS, 1% (v/v) ethanol, 5–15 $\mu$g of protein, and 0.4 mM PC containing dipalmitoylglycero-3-P-[methyl-$^3$H]choline in a final volume of 100 $\mu$l. The substrate was prepared by mixing 1.0 $\mu$HCi of radiolabeled PC with 4 $\mu$mol of unlabeled egg yolk PC in chloroform. The mixture was dried under a stream of N$_2$. The substrate was resuspended in 1 ml of H$_2$O and emulsified by sonication at room temperature. Reactions were initiated by addition of substrate and incubated for 30 minutes at 30° C. in a shaking water bath. The reaction was stopped by addition of 1 ml of 2:1 (v/v) chloroform:methanol and 100 $\mu$l of 2 M KCl followed by vigorous vortexing. The aqueous and chloroform phases were separated by centrifugation at 12,000×g for 5 minutes and, after centrifugation, a 200 $\mu$l aliqout of the aqueous was mixed with 3 ml of scintillation fluid and the release of [$^3$H]choline was quantitated by scintillation counting. For immunoblotting, protein fractions were separated in 8% SDS-PAGE gels and transferred onto polyvinylidene difluoride membranes. The membranes were blotted and incubated with antibodies (1:1000 dilution) against PLDα, β, or γ and followed by incubation with a second antibody conjugated with alkaline phosphatase. The antibody-antigen complex was visualized by assaying alkaline phosphatase activity according to a published procedure (Fan et al., 1999). The proteins recognized by antibodies were made visible by staining the phosphatase activity with a Bio-Rad immunoblotting kit. Transgenic lines containing the empty vector only were also produced and used as controls. The ABA-insensitive mutant abil-1 was provided by The Ohio State University Arabidopsis Resource Center.
Results:

Arabidopsis plants were successfully transformed using the above-described procedures. Verification of successful transformation is provided by FIG. 2 which illustrates an assay showing a nearly complete loss of PLDα activity in Arabidopsis plants having the PLDα sequence inserted in the antisense orientation in comparison to wild-type (WT) plants. This result is further verified in FIG. 3 which illustrates the results through immunoblotting of Arabidopsis leaf proteins with a PLDα-specific antibody. As shown in FIG. 3, the immunoblot of the WT Arabidopsis shows PLDα expression while Arabidopsis plants having the altered genome express no PLDα protein. Both FIGS. 2 and 3 used a 2,000×g supernatant of total leaf extracts. For FIG. 3, proteins (10 μg/lane) were separated on a 10% SDS-PAGE gel, and the PLDα band was marked with an arrow.

EXAMPLE 2

Figure 9:
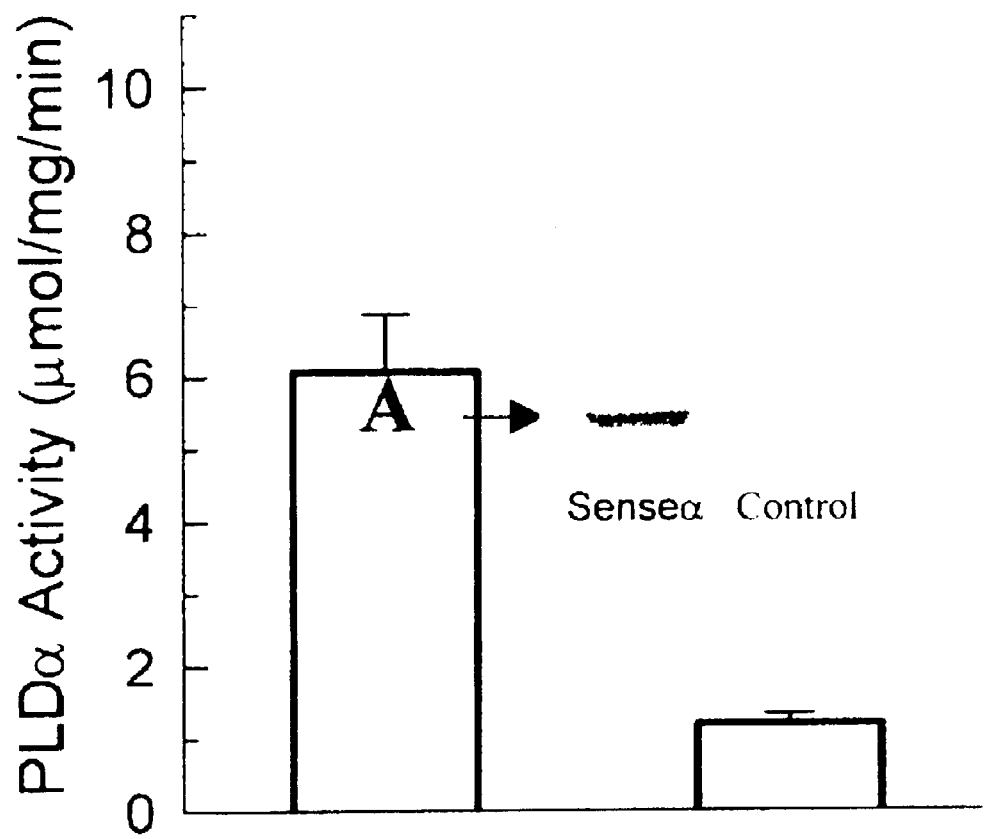
FIG. 9 is a graph illustrating PLDα activity in leaves of tobacco transformed with a sense PLDα cDNA (Sensea) or with an empty vector (Control) and the inset is an immunoblot with a PLDα-specific antibody of proteins from PLDα-overexpressing and control leaves.

This example describes the procedures used to construct transformed tobacco plants having increased levels of PLDα expression.
Materials and Methods:
Transgenic Tobacco Production and Growth A 2.8 kb cDNA fragment corresponding to SEQ ID No. 2 and encoding the full length amino acid sequence of castor bean PLDα was inserted into the *Agrobacterium tumefaciens* transfer vector pKYLX7 in the sense orientation. Again, the the insert was under the contol of the cauliflower mosaic virus 35S promoter. The T-DNA regions of the transfer vector were introduced into tobacco plants (*Nicotiana tabacum*) through Agrobacterium-mediated gene transfer via strain EHA105. Transformation of the tobacco was achieved through leaf disc inoculation. The overexpression of PLDα was confirmed by assaying PLDα activity and immunoblotting with PLD-isoform-specific antibodies according to published procedures, as described above in Example 1. Transgenic lines containing the empty vector only also were produced and used as controls. Unless stated otherwise, plants were grown under 12-hr-light/dark cycles with cool-white fluorescent light of 100 μmol m$^{-2}$ sec$^{-1}$ at 22±1° C. and 60% relative humidity.
Results:

Tobacco plants containing the insert exhibit increased expression of PLDα as shown in FIG. 9 wherein the tobacco containing the PLDα containing insert (the PLDα overexpressing tobacco) exhibited nearly six times as much PLDα activity as a tobacco plant containing the empty vector. Additionally, FIG. 9 contains an immunoblot located in the inserted portion of this figure. As shown by this immunoblot, the control plant expressed little or no PLDα while the plant containing the PLDα-sense insert expressed a much greater amount of PLDα. Thus, FIG. 9 shows that the band corresponding to tobacco having PLDα overexpression is much darker and thicker than that of the control tobacco.

EXAMPLE 3

Figure 1B:
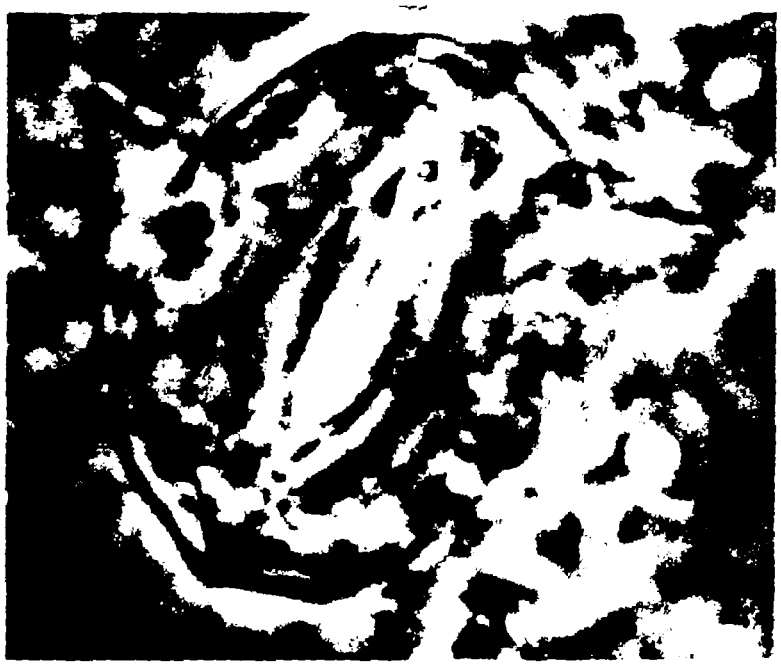
Figure 1C:
Figure 2:
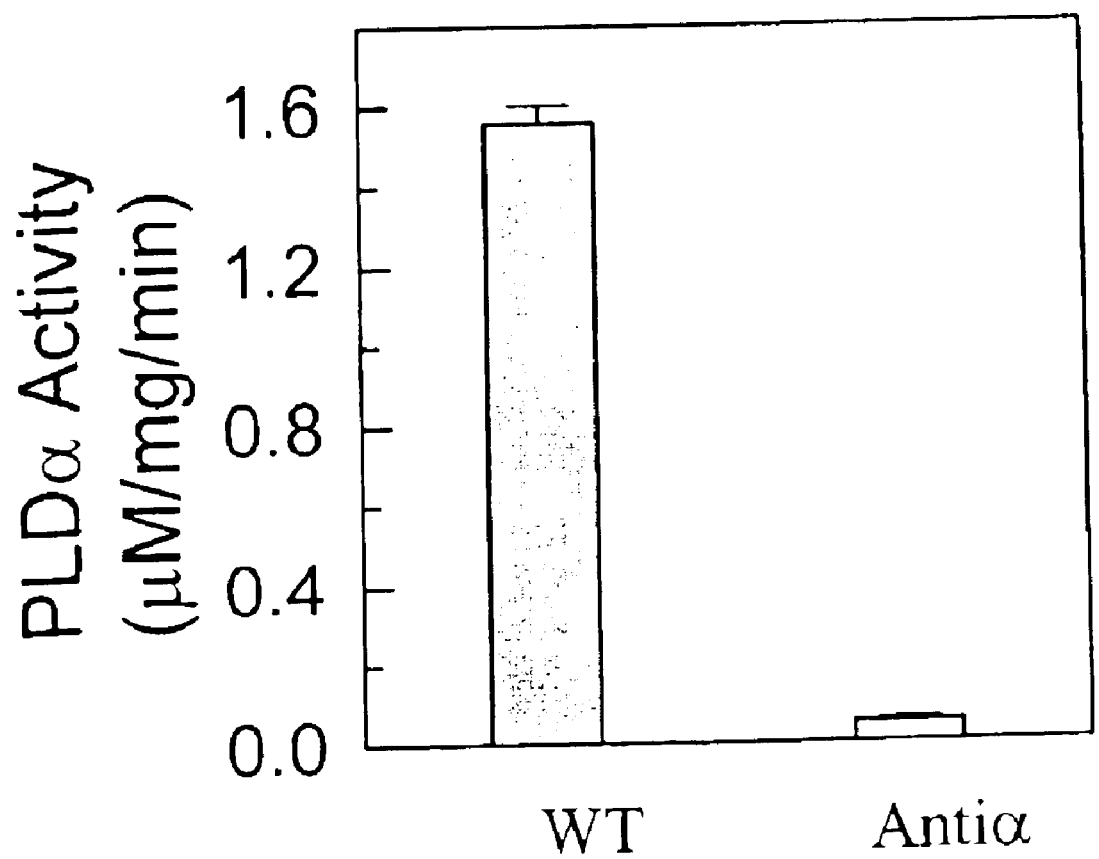
FIG. 2 is a graph illustrating PLDα activity in PLDα-antisense (Antia) and wild-type (WT) Arabidopsis leaves.
Figure 3:
FIG. 3 is a photo illustrating protein immunobloting of leaf proteins with a PLDα-specific antibody.
Figure 3:

Results from this example illustrate that different isoforms of PLD are present in Arabidopsis guard cells.
Materials and Methods:
Immunocytochemical Labeling of PLD After 4–5 weeks of growth, fully expanded Arabidopsis leaves were detached. Epidermal peels were collected from the abaxial side of Arabidopsis leaves immediately following detachment and incubated for 1 hour in a solution containing 5 mM MES-KOH (pH 6.1), 22 mM KCl, and 1 mM CaCl$_2$. The peels were then fixed in 1.5% formaldehyde, 0.5% glutaraldehyde, 0.1 M PIPES, 5 mM EGTA, 2 mM MgCl$_2$, and 0.05% Triton X-100, pH 6.9 for 35 minutes with gentle shaking. The fixed peels were washed in phosphate-buffered saline (PBS) for 30 minutes with three changes of solution. Then they were spread onto microscope slides, blotted to remove excess solution, and freeze-shattered according to the procedures of Wasteneys, et al. (1997), as described above in Example 1. The peels adhered to slides were incubated with an enzyme mixture of 1% cellulase, 1% pectinase, and 2% driselase in PBS for 30 minutes at 37° C., followed by incubating with proteinase K (5 mg/ml) for 10 minutes at 37° C. The peels were permeabilized with PBS containing 1% Triton X-100 for 1.5 hours, incubated in PBS containing 50 mM glycine for 30 minutes, and blocked in PBS containing 3% BSA for 30 minutes. Then they were incubated with antibodies to PLDα or its preimmune sera at 4° C. overnight, followed by incubation for 20 minutes at room temperature. All antibodies were diluted 1:100 in the blocking solution. The slides were rinsed and then incubated for 2 hrs with a second antibody (1:50 dilution), which was conjugated to an alkaline phosphatase (Sigma). After rinsing, slides were incubated at room temperature for 20 minutes with the phosphatase substrate fast red/naphthol that contained 0.6 mM levamisole to block endogenous AP activity from tissues. The slides were rinsed three times with PBS and sealed for observation and photographing using an Olympus BH-2 microscope.
Results:

The results for this example are given in FIGS. 1–3. In photo A of FIG. 1, PLDα labeled with PLDα antibody was clearly detectable in guard cells, whereas PLDα labeled with PLDα pre-immune serum was not so detectable (it gave a negligible background) as shown in photo B. Labeling specificity for PLDα was verified unequivically by the absence of immuno-staining in guard cells from PLDα-depleted plants, shown in photo C. Antisense suppression of PLDα resulted in a nearly complete loss of PLDα in Arabidopsis leaves as indicated by the absence of PLDα activity, shown in FIG. 2, and protein, shown in FIG. 3. The presence of PLDα in guard cells was confirmed using fluorescence confocal imaging and immuno-gold electron microscopy. These results establish that PLDα is localized in guard cells and that the expression of PLDα in guard cells is suppressed in PLDα antisense plants.

EXAMPLE 4

This example describes methods used to determine stomatal movement in Arabidopsis plants and provides results from the use of such methods.
Materials and Methods:
Stomatal Aperture and Drought Treatments Detached Arabidopsis leaves were floated with the abaxial side downward in a solution containing 5 mM MES-KOH (pH 6.1), 22 mM KCl, and 1 mM CaCl$_2$ for 1 hour under the same light conditions used for growing plants. Leaves then were incubated without or with ABA at indicated concentrations. ABA was made as a 10 mM stock solution in 5% dimethyl sulfoxide (DMSO), and the same amount of DMSO (0.005%) was also added to the control solution in all treatments. Stomatal aperture was measured as diffusion resistance with a steady state porometer (Li-COR 1600, Lincoln, Nebr.). The porometer was set for aperture of 0.5 cm$^2$, pressure of 100 pa, and relative humidity of 30%. Changes in diffusion resistance were monitored on plants at indicated time intervals.

Figure 6:
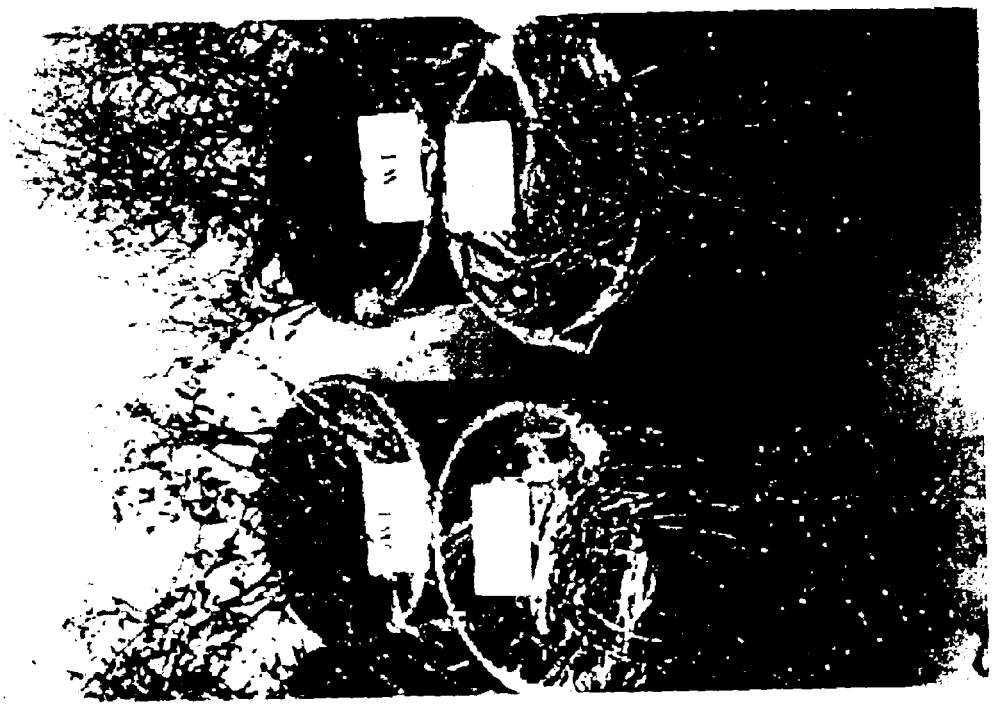
FIG. 6 is a photo illustrating drought tolerance in PLDα-depleted Arabidopsis phenotypes of PLDα-depleted (Antia) and wild-type (WT) plants after withholding irrigation for 5 days.

Before drought treatment was imposed, plants were grown in a greenhouse for 6–8 weeks and watered regularly from the tops of the pots. Soil water content in each pot was adjusted to approximately the same level before drought treatment. Plants were subjected to drought by withholding irrigation and covering the soil surface with plastic wrap. The photo shown in FIG. 6 compares four different sets of plants from this experiment after five days of drought. The plants labeled WT(drought) are wild-type plants subjected to drought. The plants labeled WT(ABA+drought) are wild-type plants subjected to drought and sprayed with ABA. The plants labeled Antia(drought) are plants containing the antisense insert after being subjected to drought for five days. Finally, the plants labeled Antia(ABA+drought) are plants containing the antisense insert after being subjected to five days of drought and having ABA treatment. Soil moisture in the 0–20 cm soil layer was monitored during drought using a time domain reflectometer (Soil Moisture Equipment Corp., Santa Barbara, Calif.). When ABA(10 $\mu$M) was sprayed on plants for some treatments, an identical amount of water was sprayed on controlled groups of plants. Leaves were collected at various times of drought treatment, and leaf water potential ($\psi_w$) was measured with a thermocouple psychrometer (Decagon Devices Inc., Pullman, Wash.).

Figure 4:
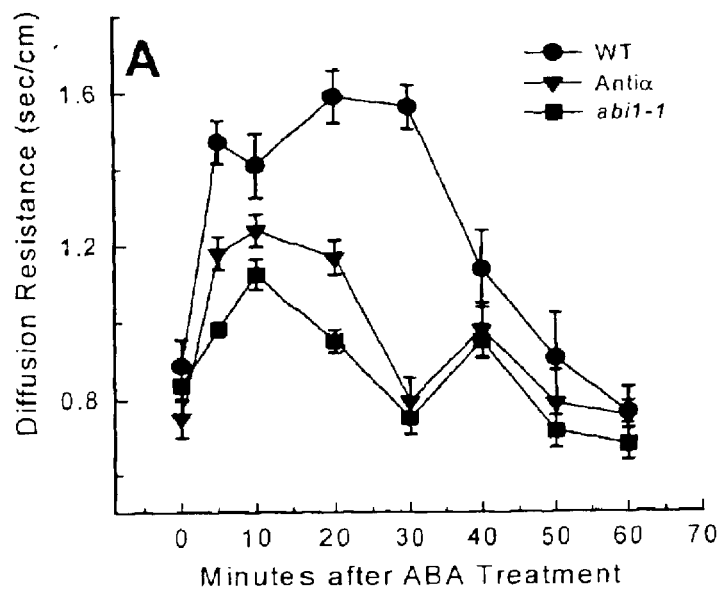
FIG. 4 is a graph illustrating a decreased response to ABA-induced stomatal closure in PLDα-depleted Arabidopsis leaves through a comparison of temporal diffusion resistance induced by 10 mM ABA in wild-type (WT), PLDα-depleted (Antia), and abi-1 Arabidopsis leaves.
Figure 5:
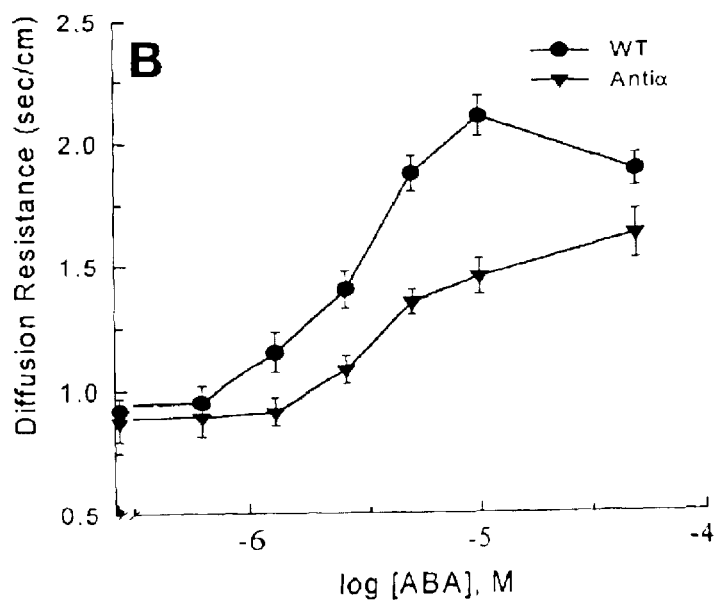
FIG. 5 is a comparative graph illustrating the effect of ABA concentrations on diffusion resistance in wild-type and PLDα-depleted Arabidopsis.

Results:

The depletion of PLDα in guard cells provides a means to assess the role of this PLD in stomatal movement. Stomatal closure was determined by measuring diffusion resistance. Under normal growing conditions, PLDα-deficient and wild-type plants grew comparably. No differences occurred in plant size, development, reproduction, or the size and density of guard cells on leaves. When leaves were incubated with 10 $\mu$M ABA, stomatal closure was induced. This result is shown by the approximately twofold increase in diffusion resistance in wild-type leaves, as shown in FIG. 4. The ABA effect persisted for more than 30 minutes in wild-type plants and then decreased. The same ABA treatment had a much smaller effect on stomatal closure in PLDα-suppressed leaves. The ABA-induced increase in diffusion resistance was approximately 50% of that observed in wild-type leaves and returned to the basal level approximately 20 minutes after ABA application. The response to ABA in PLDα-deficient leaves resembled that of the well-characterized, ABA-insensitive mutant abi-1, which is defective in a protein (phosphatase 2C) involved in ABA signaling in Arabidopsis guard cells. As shown in FIG. 5, in the range of 0.5–50 $\mu$M ABA tested, the PLDα-depleted leaves exhibited a lower diffusion resistance than that of wild-type leaves. The 2 $\mu$M concentration of ABA stimulated stomatal closure in wild-type leaves but had no effect in PLDα-suppressed leaves. These results demonstrate that PLDα-deficient leaves are less sensitive to ABA.

Figure 7:
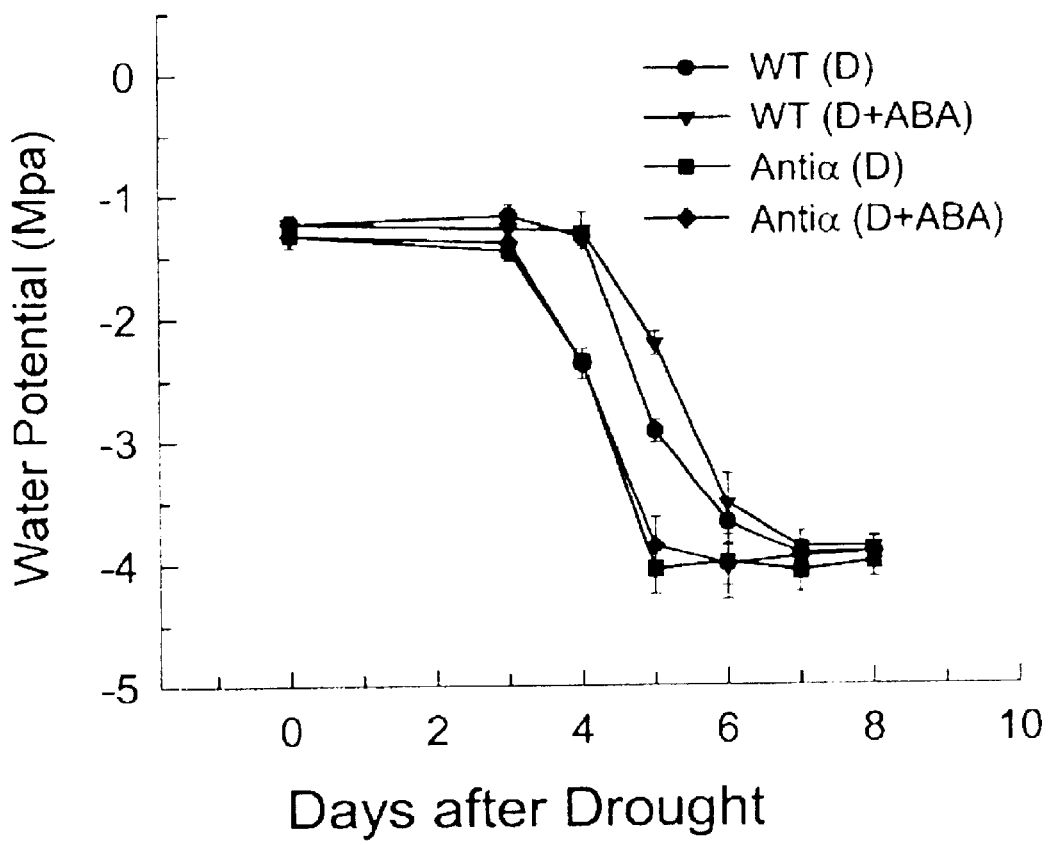
FIG. 7 is a graph comparing the decrease in leaf water potential during drought conditions.
Figure 8:
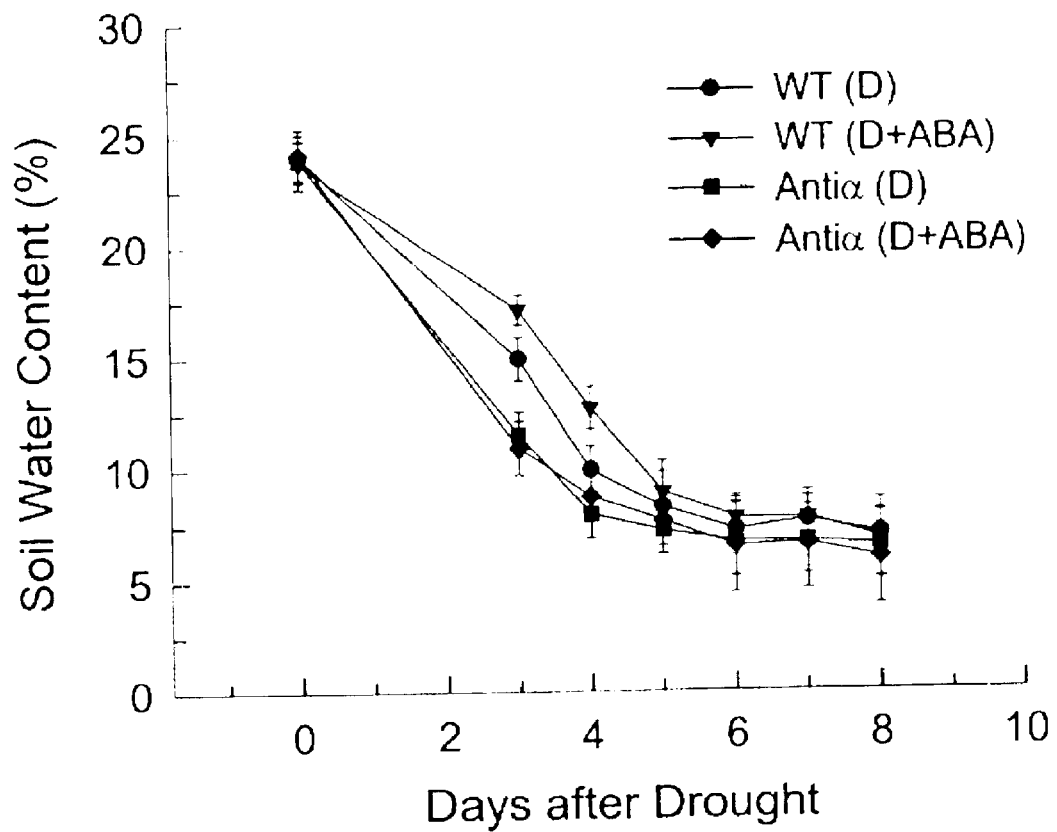
FIG. 8 is a graph comparing the decrease in soil water content during drought conditions.

As shown by FIG. 6, wild-type plants can withstand drought conditions better than plants having the antisense insert into their genome. Additionally, treatment with ABA improves this drought resistance. Additional support for this conclusion is provided in FIGS. 7 and 8 which compare the decrease in leaf water potential (FIG. 7) and soil water content (FIG. 8). As shown by these graphs, plants having the antisense insert have decreased leaf water potential and deplete the water contained in soil at a much higher rate.

EXAMPLE 5

This example describes methods used to determine stomatal movement in tobacco plants and provides results from the use of such methods.

Materials and Methods:

Stomatal Aperture and Drought Treatments

For measuring leaf diffusion resistance directly on tobacco plants, ABA at indicated concentrations (2.5 $\mu$M and 5 $\mu$M) was sprayed onto leaves of approximately 2-month-old plants. Changes in diffusion resistance were monitored on plants at indicated time intervals. ABA was made as a 10 mM stock solution in 5% dimethyl sulfoxide (DMSO), and the same amount of DMSO (0.005%) was also added to the control solution in all treatments. Stomatal aperture of detached leaves was measured as diffusion resistance with a steady state porometer using the method of Thimann and S. O. Satler, *Relation Between Leaf Senescence and Stomatal Closure: Senescence in Light*, 76 Proc. Natl. Acad. Sci. USA, 2295–2298 (1979), the methods and teachings of which are hereby incorporated by reference. Detached Arabidopsis leaves were floated with the abaxial side downward in a solution containing 5 mM MES-KOH (pH 6.1), 22 mM KCl, and 1 mM $CaCl_2$ for 1 hour under the same light conditions used for growing plants. Leaves were then incubated with or without ABA at the indicated concentrations. ABA was made as a 10 mM stock solution in 5% dimethyl sulfoxide (DMSO), and the same amount of DMSO (0.005%) was also added to the control solution in all treatments. Stomatal aperture leaves was measured by using a diffusion porometer (Lambda Instruments LI-1600). During measurement, the porometer was set for aperture at 0.5 $cm^2$, pressure at 100 kPa, and relative humidity at 30%. For tobacco plants, leaf diffusion resistance was also measured in leaves attached to approximately 2-month-old plants following foliar spraying of ABA at indicated concentrations. Changes in diffusion resistance in response to ABA in both detached and intact leaves were monitored at indicated time intervals.

When ABA (10 $\mu$M) was sprayed on plants in some treatments, control groups of plants were sprayed with water in the same amount as for the ABA treatment. Leaves were collected at various times during drought treatment, and leaf water potential ($\psi_w$) was measured with a thermocouple psychrometer. To measure the rates of water loss from tobacco, leaves were detached and left in ambient conditions. Decreases in fresh weight were recorded as a function of time, and the percentages of decreases were expressed as percent water loss.

Figure 10:
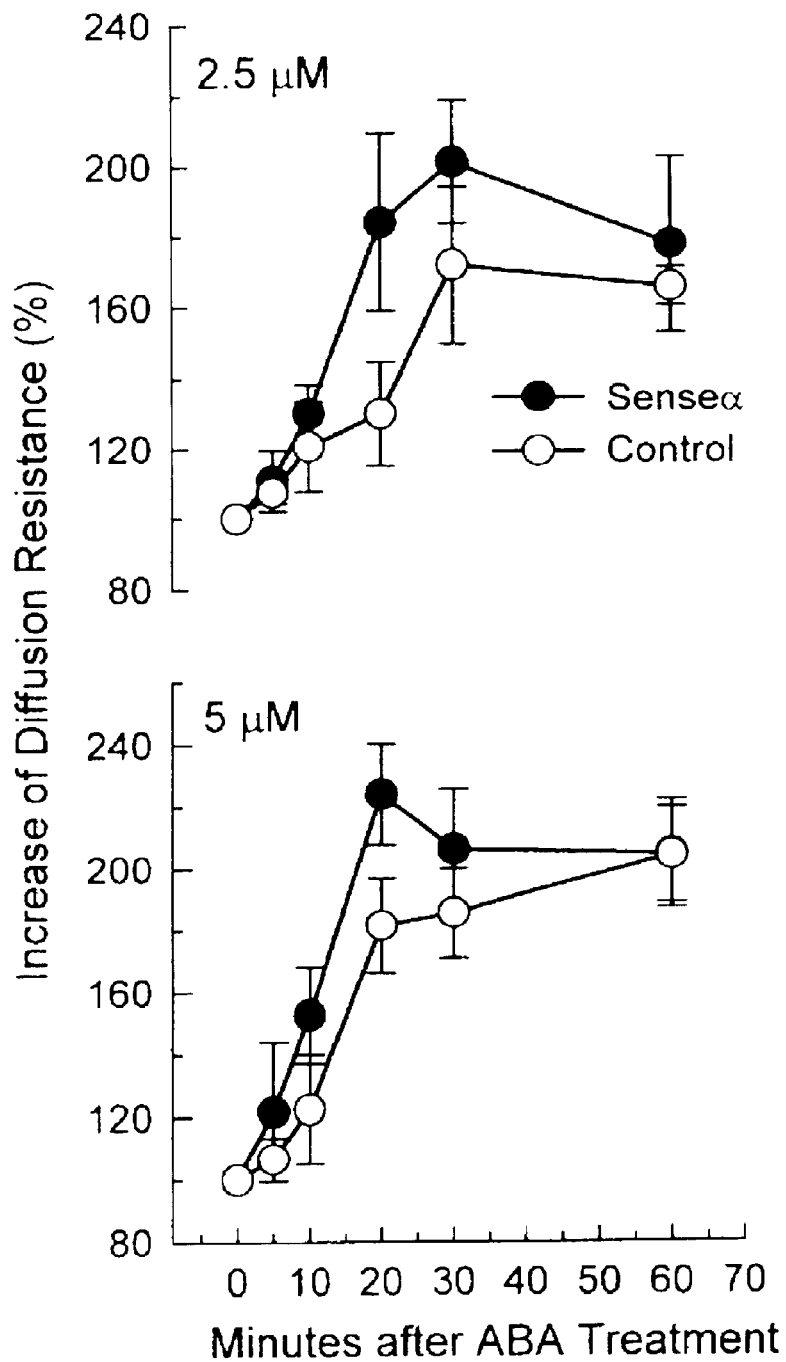
FIG. 10 is a comparative graph illustrating ABA-induced increase in diffusion resistance in PLDα-overexpressing and control tobacco leaves.
Figure 11:
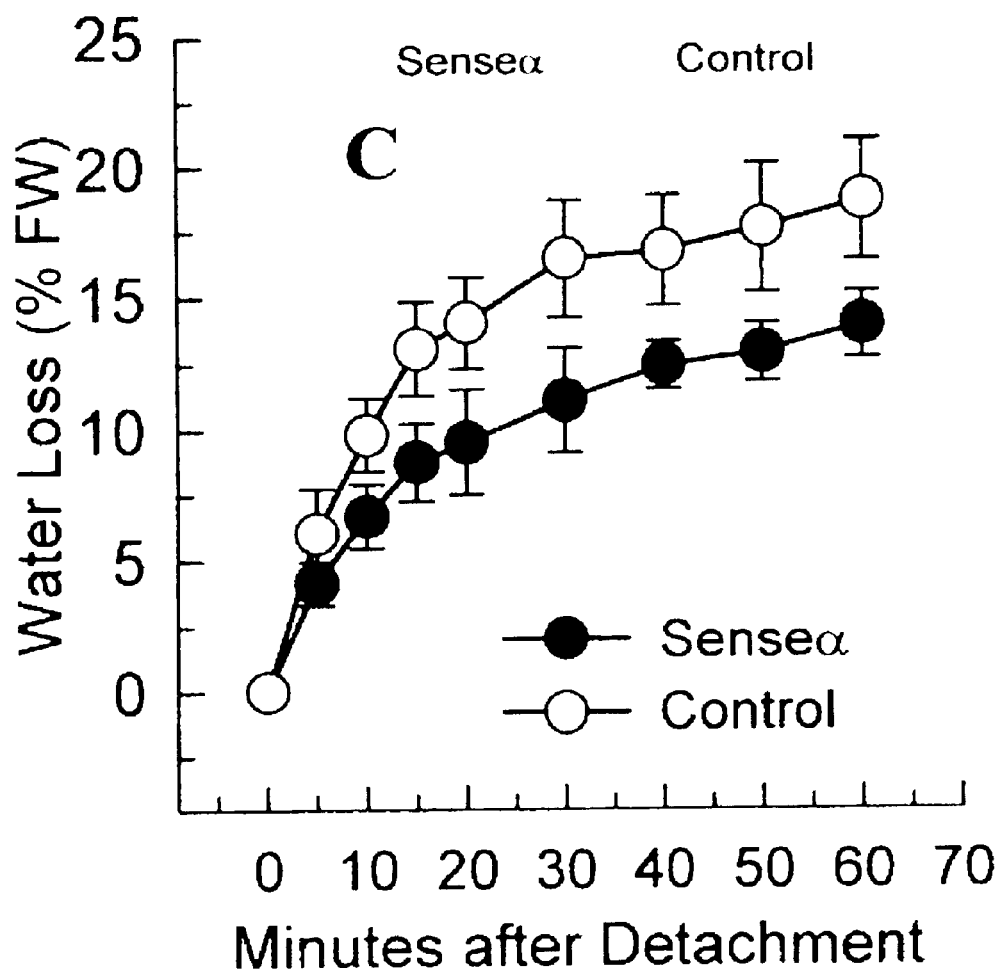
FIG. 11 is a graph illustration water loss from detached leaves of PLDα-overexpressing and control tobacco plants.

Results:

Results for this example are given in FIGS. 10 and 11. As shown in FIG. 10, PLDα overexpressing tobacco possesses a higher diffusion resistance and a longer period of sensitivity to ABA treatment in comparison to control tobacco plants which contain an empty vector. Leaf diffusion resistance increased approximately 80% in PLDα-overexpressing plants while diffusion resistance in control plants increased only about 30%. Further treatment with ABA increased diffusion resistance in both sets of tobacco plants. These differences demonstrate that overexpression of PLDα contributes to stomatal closure in plants and increases plant sensitivity to ABA. This will provide plants with decreased transpiration rates and increased resistance to drought.

EXAMPLE 6

This example descibes methods used to compare PLDα overexpressing tobacco plants with tobacco plants containing an empty vector after all plants were subjected to drought conditions.

Materials and Methods:

Four six week-old tobacco plants of similar size were subjected to drought conditions by withholding irrigation for 15 days. The plants were all grown in a growth room with cool-white fluorescent lights at 23±2° C. and 45% relative humidity. Two of the plants had been transformed with the antisense vector prepared in Example 1 while the remaining two plants were transformed with an empty vector. Results for this example are given in FIG. 12.

Figure 12:
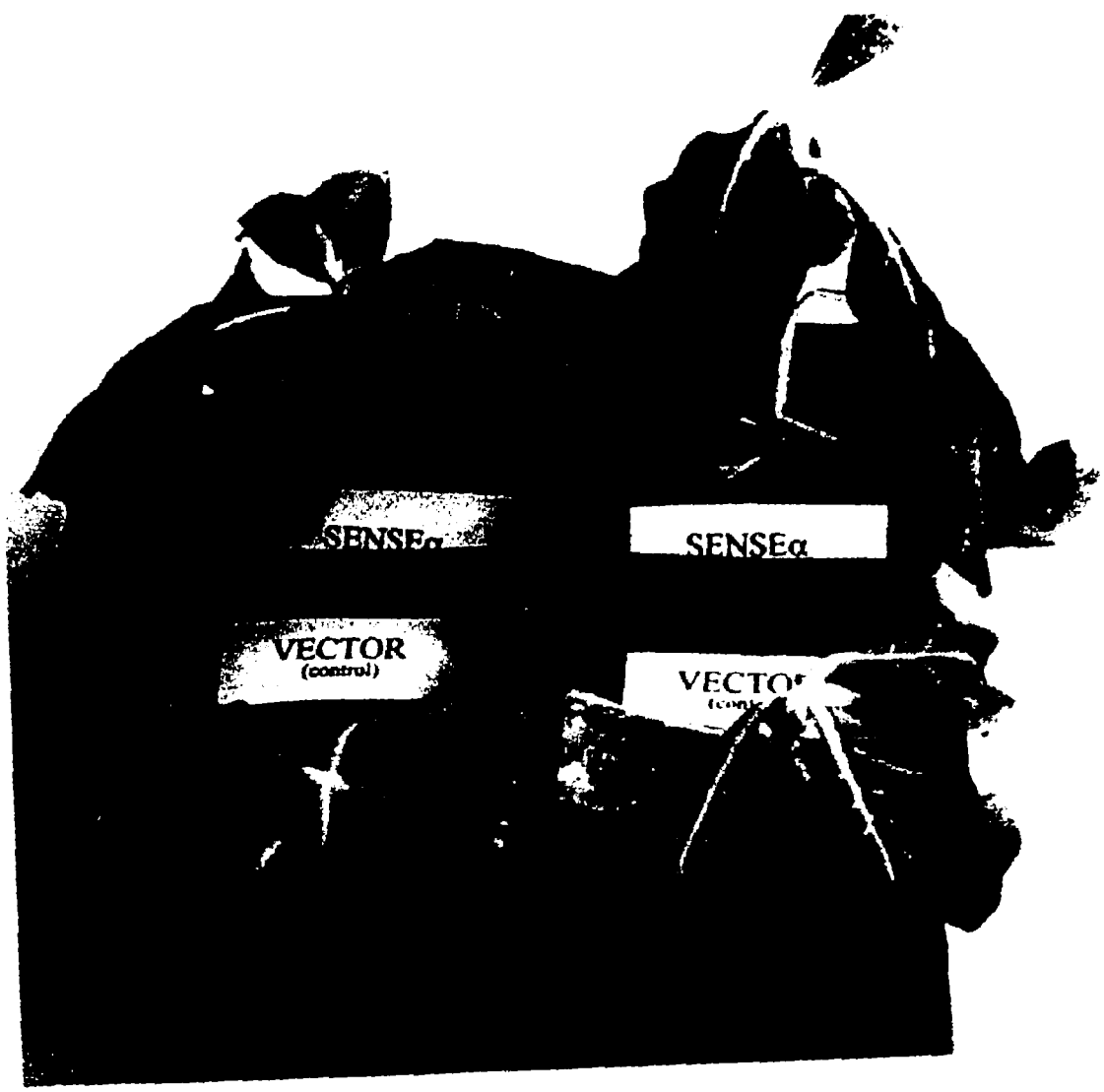
FIG. 12 is a photograph showing PLDα overexpressing tobacco plants and tobacco plants containing an empty vector after 15 days of drought conditions.

Results:

As shown in FIG. 12, PLDα overexpressing tobacco plants exhibit increased drought tolerance as evidenced by their increased turgidity. These PLDα overexpressing plants are the two plants at the top of FIG. 12. Plants transformed with the empty vector (the two plants in the bottom of FIG. 12) appear much more wilted than their PLDα overexpressing counterparts. This further verifies PLD's role in water conservation of plants.

We claim:

1. A method of growing a transformed plant in a location having unsuitable water and growth conditions for said plant's growth prior to transformation, said method comprising the steps of:

recombinantly altering the genome of said plant to change the level of PLD-α expressed by said plant, wherein the genome is altered by introducing a PLD-α coding sequence in antisense orientation to decrease the level of PLD-α in the plant, or by introducing a PLD-α coding sequence in sense orientation to increase the level of PLD-α in the plant;

testing water consumption levels of said plant in order to determine if said genome alteration will permit plant growth in said location; and planting the progeny of said plant in said location.

2. The method of claim 1, wherein the PLD-α coding sequence is introduced in antisense orientation and PLD-α levels are decreased in said plant.

3. The method of claim 1, wherein PLD-α coding sequences are introduced in sense orientation and PLD-α levels are increased in said plant.

4. The method of claim 2, said PLD-α coding sequence in antisense orientation having the sequence of SEQ ID No. 1.

5. The method of claim 3, wherein said PLD-α coding sequences are operably linked to the CaMV 35S promoter.

6. The method of claim 3, said PLD-α coding sequences having the sequence of SEQ ID No. 2.

7. The method of claim 1, said testing including determining said plant's transpiration rate.

8. The method of claim 1, said testing including measuring said plant's diffusion resistance.

9. The method of claim 1, further comprising the step of exposing said plant to abscisic acid.

10. The method of claim 1, said testing including subjecting said plants to drought conditions.

11. The method of claim 1, said testing including observing said plant's turgidity.

12. A method of growing a transformed plant having modified stomatal closure responses to water availability, which plant in its untransformed state exhibits a first stomatal closure response, said method comprising the steps of:

recombinantly altering the genome of said plant to change said fist level of stomatal closure response, said altering resulting in a modified level of PLD-α expression, wherein the genome is altered by introducing a PLD-α coding sequence in antisense orientation to decrease the level of PLD-α in the plant, or by introducing a PLD-α coding sequence in sense orientation to increase the level of PLD-α in the plant; and testing said stomatal closure responses of said transformed plant to determine if said plant has modified stomatal closure responses.

13. The method of claim 12, wherein the PLD-α coding sequence is introduced in antisense orientation and PLD-α levels are decreased in said plant.

14. The method of claim 12, wherein PLD-α coding sequences are introduced in sense orientation and PLD-α levels are increased in said plant.

15. The method of claim 13, said PLD-α coding sequence in antisense orientation having the sequence of SEQ ID No. 1.

16. The method of claim 14, wherein said PLD-α coding sequences are operably linked to the CaMV 35S promoter.

17. The method of claim 14, said PLD-α coding sequences having the sequence of SEQ ID No. 2.

18. The method of claim 12, said testing including determining said plant's transpiration rate.

19. The method of claim 12, said testing including measuring said plant's diffusion resistance.

20. The method of claim 12, further comprising the step of exposing said plant to abscisic acid.

21. The method of claim 12, said testing including subjecting said plants to drought conditions.

22. The method of claim 12, said testing including observing said plant's turgidity.

23. A method of altering water consumption by a plant comprising the step of manipulating the level of PLD-α enzyme expression and thereby altering water consumption, wherein the level of PLD-α enzyme expression level is manipulated by introducing a PLD-α coding sequence into the plant in antisense orientation to decrease the level of PLD-α in the plant, or by introducing a PLD-α coding sequence in sense orientation into the plant to increase the level of PLD-α in the plant.

24. The method of claim 23, wherein the PLD-α coding sequence is introduced in antisense orientation and PLD-α levels are decreased in said plant.

25. The method of claim 23, wherein PLD-α coding sequences are introduced in sense orientation and PLD-α levels are increased in said plant.

26. The method of claim 25, said PLD-α coding sequence in antisense orientation having the sequence of SEQ ID No. 1.

27. The method of claim 25, wherein said PLD-α coding sequences are operably linked to the CaMV 35S promoter.

28. The method of claim 25, said PLD-α coding sequences having the sequence of SEQ ID No. 2.

29. The method of claim 23, further comprising the step of measuring said plant's water consumption.

30. The method of claim 29, said measuring including determining said plant's transpiration rate.

31. The method of claim 29, said measuring including measuring said plant's diffusion resistance.

32. The method of claim 23, further comprising the step of exposing said plant to abscisic acid.

33. The method of claim 29, said measuring including subjecting said plants to drought conditions.

34. The method of claim 29, said measuring including observing said plant's turgidity.

* * * * *

SEQUENCE LISTING

<160> NUMBER OF SEQ ID NOS: 2

<210> SEQ ID NO 1
<211> LENGTH: 783
<212> TYPE: DNA
<213> ORGANISM: Arabidopsis thaliana

<400> SEQUENCE: 1

```
tgttccaaga gaccacgatg tgtggaatgt ccaattgttt aggtccattg atggaggagc      60
tgctgctggg tttcccgagt cgcctgaagc tgctgcggaa gccgggcttg tacagtggga     120
aagataacat cattgatagg agtatccaag atgcttacat tcatgcaatc agacgtgcta     180
aggatttcat ctacgttgaa aaccagtact tccttgggga ttcttttgct tgggcagccg     240
atggtattac tcctgaggac atcaatgccc tgcacttaat cccaaaagag ttgtcgctga     300
agatagttag caagattgat caaggagaga agttcagggt ctatgttgtg gttccaatgt     360
ggccagaagg tctcccagag agtggatcag tgcaagctat attagactgg cagaggagga     420
ccatggagat gatgtacaag gatgtgattc aggctctcaa gggtcttgag ggcccggaag     480
atccaagaaa ctatctgaca ttcttctgtc ttggaaaccg tgaggtcaag aaagatggag     540
agtatgagcc tgctgagaaa ccagaccccg acactgatta catgagggcg caagaagcac     600
gccgtttcat gatttacgtc cacaccaaaa tgatgatcgt tgacgatgaa tacattatca     660
ttgggtctgc taacatcaac cagaggtcaa tggacggtgc aagagactct gagatagcaa     720
tgggaggtta tcaaccacat cacttgtccc atagacaacc agctcgtggc cagatccatg     780
ggt                                                                   783
```

<210> SEQ ID NO 2
<211> LENGTH: 2808
<212> TYPE: DNA
<213> ORGANISM: Ricinus communis

<400> SEQUENCE: 2

```
cttcgtttca cattctctgt acttttacga ttacgcgcat acaaaattat tttatttgat      60
atatacatac acacggagct aagatcggat cagatcacag aaattctctc attctcagat     120
ctctctctgt ttctcttcat catcataaat ttacaagtga gaaatggcgc agatatcttt     180
gcacggaact ctacatgtaa cgatctatga ggtggataag cttcacagcg gaggtggtcc     240
ccacttcttt cgtaagcttg ttgaaaatat tgaggagaca gttggttttg gcaaaggagt     300
tagtaaactc tatgcaacta ttgacctaga aaaggctaga gttggaagga ctagaatact     360
ggaaaatgaa caatccaacc ccaggtggta tgagtccttt cacgtttatt gtgctcatca     420
ggcttcaaat gtaatattca cagtcaagga tgataatcct attggggcca ccttaattgg     480
aagagcatat gtaccagttg aagagctcct agatggagaa gagatagata ggtgggttga     540
gatattggat gaagacaaga accccgtcca tagtggttct aagatccatg tgaaactgca     600
gtactttgag gttaccaagg accgtaactg gggacagggt atcagaagtt caaaatatcc     660
tggagtacct tatacatact tctcgcagag acaaggatgt aaggtttctc tctaccaaga     720
tgctcatatt ccagacaaat tgttcctca aattcctctt gctggaggca attactatga     780
gcctcacagg tgctgggaag atgtttttga tgcaattacc aatgcaaaac acttgatcta     840
catcactggc tggtctgttt atactgaaat ctccttaata agggactcga ggaggccaaa     900
gccaggagga gatatcaccc taggtgagct gcttaagaag aaggcaagtg aaggtgttag     960
```

```
ggtccttatg ctggtgtggg atgacagaac ctccgttggt ttattgaaaa aggatggact    1020
catggcaact catgatgagg agactgaaca tttcttccag aatactgatg tgcattgtgt    1080
gctgtgtcct cgaaatcctg atgatggtgg aagctttgtt caggatctac aaatctctac    1140
tatgttcact catcaccaga agattgtggt ggtggacagt gcaatgccta atggagattc    1200
gcagaggagg agaattgtca gttttgttgg gggtctcgac ctctgtgatg ggagatatga    1260
ttccccattc cattcccttt tcaggacact ggattcggca caccatgatg attttcatca    1320
gcccaacttt gctggtgctt caattgaaaa aggtggtcca agagaacctt ggcatgacat    1380
ccactccaga cttgaaggac caattgcttg ggatgttttg tttaattttg agcagagatg    1440
gagaaagcaa ggtggtaaag acctgctcat tcagctgaga gaactagaag atgttatcat    1500
tcccccatct cctgttatgt atcctgatga ctttgaggca tggaatgtcc agttgtttag    1560
atccattgat ggtggagctg catttggttt ccctgagaca cctgaagatg cgccagaggc    1620
tgggcttgtc agtggaaagg ataacatcat tgaccgaagt attcaggatg cttatatcca    1680
tgccattcga agggcaaaga attttattta tattgaaaat cagtatttcc ttggaagttc    1740
ttttggttgg agtcctgatg gtattaagcc tgaggatatt aatgcactgc atctaatacc    1800
caaggaactt tcactcaaga tacttagcaa gattgcggca ggggagaggt tcactgttta    1860
cattgttgtt ccaatgtggc cagagggtat accagagagt gcatcagttc aggctatatt    1920
agattggcag aagaggacaa tggaaatgat gtataaagat attgtgcagg ctctcaaagc    1980
caatggaatt attgaggatc ctcggaacta tctgacattc ttctgccttg gtaaccgcga    2040
agtgaagaag agtggtgaat atgaacctgc agaaaaacca gagcctgata cagactatat    2100
aagagctcag gaggccagac gtttcatgat ttatgttcat acaaagatga tgattgtcga    2160
tgatgagtac attataattg gatctgccaa catcaaccag agatcaatgg atggtgctag    2220
agactccgaa atagccatgg gagcctatca accacatcac ttgtcaacca ggcagccagc    2280
acgaggtcag atccatggtt tccgtatgtc attatggtac gaacaccttg gcatgctcga    2340
cgagtcattc cttaatccag aaagtgagga gtgtgtcaga aaggtgaacc agatggcaga    2400
aaaatattgg gatctctatt caagcgagac actggaacat gacctacctg gtcatttgct    2460
ccggtatcct attggggtcg ctagtgaagg agatgtcaca gagctccctg gaaccgagtt    2520
tttccctgac acgaaggctc gtgttctagg tgctaaatcc gattaccttc ctcccatcct    2580
gacaacttaa tggaactcta agcagttctc gaagaattac ctgccttgcc agcccattta    2640
tgttactagt tgtagccaga aaataaatca tgtatcgcca ttctatccat aatgtttttg    2700
tgccaggatt ggggtatcag gattgacaga tgtgtcactg ctgtggtgtg gtgtgatgct    2760
gtctatgttg aactttgttt atctaatcca tgtcttttc tacaaaac    2808
```